United States Patent [19]
Bailey et al.

[11] Patent Number: 5,128,517
[45] Date of Patent: Jul. 7, 1992

[54] TEMPERATURE CONTROLLED FLUID CIRUCLATING SYSTEM

[75] Inventors: David F. Bailey; John T. Ray, both of Hillsborough County, Fla.

[73] Assignee: Hollister, Inc., Libertyville, Ill.

[21] Appl. No.: 655,131

[22] Filed: Feb. 14, 1991

Related U.S. Application Data

[63] Continuation of Ser. No. 477,340, Feb. 8, 1990, Pat. No. 5,051,562.

[51] Int. Cl.[5] ................................................ H05B 1/02
[52] U.S. Cl. ................................. 219/506; 219/497; 219/490; 392/471
[58] Field of Search ............. 219/506, 497, 494, 488, 219/490, 508–510; 307/117; 392/471

[56] References Cited

U.S. PATENT DOCUMENTS

| | | | |
|---|---|---|---|
| 3,988,577 | 10/1976 | Leitner et al. | 219/506 |
| 4,101,874 | 7/1978 | Dennison et al. | 219/309 |
| 4,314,143 | 2/1982 | Bilstad et al. | 219/506 |
| 4,343,987 | 8/1982 | Schimoke et al. | 219/506 |
| 4,371,779 | 2/1983 | Maynard | 219/309 |
| 4,467,178 | 8/1984 | Swindle | 219/506 |
| 4,633,066 | 12/1986 | Chang | 219/506 |

*Primary Examiner*—Mark H. Paschall
*Attorney, Agent, or Firm*—Arthur W. Fisher, III.

[57] ABSTRACT

A temperature control system for use with a fluid circulating system operable in a heating or cooling state to monitor and control the temperature and flow of fluid circulated through a remote liquid circulation manifold comprising a display/control panel to select the system operating parameters and provide a visual indication of the system status including operating temperature and fluid flow and a micro control including logic circuitry to receive input signals from the display/control panel and fluid circulating system and to generate system control signals to control the operation of the fluid circulating system and system indicator signals to provide the visual indication of system operations.

17 Claims, 21 Drawing Sheets

TEMPERATURE CONTROLLED FLUID CIRUCLATING SYSTEM

COPENDING APPLICATION

This application is a continuation application of pending application Ser. No. 477,340, filed Feb. 8, 1990 now U.S. Pat. No. 5,051,562.

BACKGROUND OF THE INVENTION

1. Field of the Invention

A temperature control system for use with a fluid circulating system operable in a heating or cooling state to control the temperature and flow of fluid circulated through a remote liquid circulating manifold.

2. Description of the Prior Art

Thermal blankets and heating pads are well known in the art. Such thermal blankets commonly include either a cooling or heating effect. Generally heating blankets or pads incorporated the use of electrical resistance elements disposed thereout the area of the blanket. Similarly cold applicator pads or blankets used in the medical field frequently include a flexible plastic package containing two chemicals which when mixed together absorb heat. The chemicals are frequently packaged on either side of a rupturable membrane so that application of pressure to the exterior package ruptures the membrane and causes the fluids to mix and produces the heat absorbing reaction. Alternately, cooling pads may be used in combination with a compressor, refrigerant condensation and evaporator coils. It is obvious that the above type cold pads or blankets are heavy and cumbersome.

With reference to heat type thermal blankets used in the medical field, structures have been developed to circulate a heated fluid through a duct in the pad or blanket. Such structure are designed to overcome the obvious inefficiencies and disadvantages associated with the structures involving heating resistance wires embedded in the blanket or pad.

It is recognized that the use of fluid in a both a heating and cooling thermal blanket or pad is much desirable over the aforementioned prior art structures. However such a structure does include certain disadvantages. U.S. Pat. No. 3,894,213 to Kumar and Brown and U.S. Pat. No. 3,967,627 are examples of prior art structures which while operational appear to be bulky, less than reliable and do not have certain safeguards involved with the application of selected and variable temperature ranges which would be highly desirable.

In contrast, U.S. Pat. No. 4,459,468 discloses a circulating system capable of producing both a heated and cooled fluid of various temperatures circulated to the thermal blanket at the desired "hot" or "cold" temperature. The system comprises a reservoir and a temperature transfer means to heat or cool fluid within the reservoir. A temperature sensor monitors the fluid temperature in the reservoir. A temperature control means is electrically connected in current regulating and activating relation to the temperature transfer means such that a continuous path of information flows between the monitored fluid and temperature control means and to the thermal modules for activation thereof in order to maintain the desired temperature.

SUMMARY OF THE INVENTION

The present invention relates to a temperature control system comprising a system indicator means, system sensor means and systems control means as described more fully hereinafter for use with a fluid circulating system similar to the temperature control fluid circulating system disclosed in U.S. Pat. No. 4,459,468.

The fluid circulating system comprises a fluid reservoir coupled to a pump and a thermal blanket or similar remote liquid circulation manifold to selectively circulate fluid to and from the remote liquid circulating manifold. The operation of thermal modules, disposed in thermal transfer relationship with the fluid reservoir, is controlled by a micro control and a display/control panel. The fluid circulating system further includes a remote temperature sensor, including means to generate a remote temperature signal corresponding to the temperature at the remote site and a fluid flow control device including means to selectively direct the output of the pump to the fluid reservoir or remote liquid circulating manifold, fluid flow sensor including means to detect fluid flow and means to generate a fluid flow signal in response thereto, system warning indicator and power supply. a fluid level sensor including means to generate a fluid level signal when the fluid level reaches a predetermined minimum level and fluid temperature sensor including means to generate a fluid temperature signal corresponding to the fluid temperature are operatively disposed within the fluid reservoir; while, a thermostat is operatively disposed within the fluid flow control device.

The display/control panel is mounted on a cabinet as that operatively houses or supports the pump, thermal modules, fluid reservoir, micro control, fluid flow control device, flow sensor, system warning indicator 28 and power supply.

The display/control panel comprises a temperature display section, fluid status section and switch control section to continuously monitor the system control, monitor and display the system operating conditions.

With power ON, the operating mode and temperature are selected by using the switch control section. With the pump ON liquid will normally circulate through the fluid circulating system.

The micro control includes means to control and alter system operations through operator control or when a system malfunction is sensed.

The inventon accordingly comprises the features of construction, combination of elements, and arrangement of parts which will be exemplified in the construction hereinafter set forth, and the scope of the invention will be indicated in the claims.

BRIEF DESCRIPTION OF THE DRAWINGS

For a fuller understanding of the nature and object of the invention, reference should be had to the following detailed description taken in connection with the accompanying drawings in which:

Figure 9A:
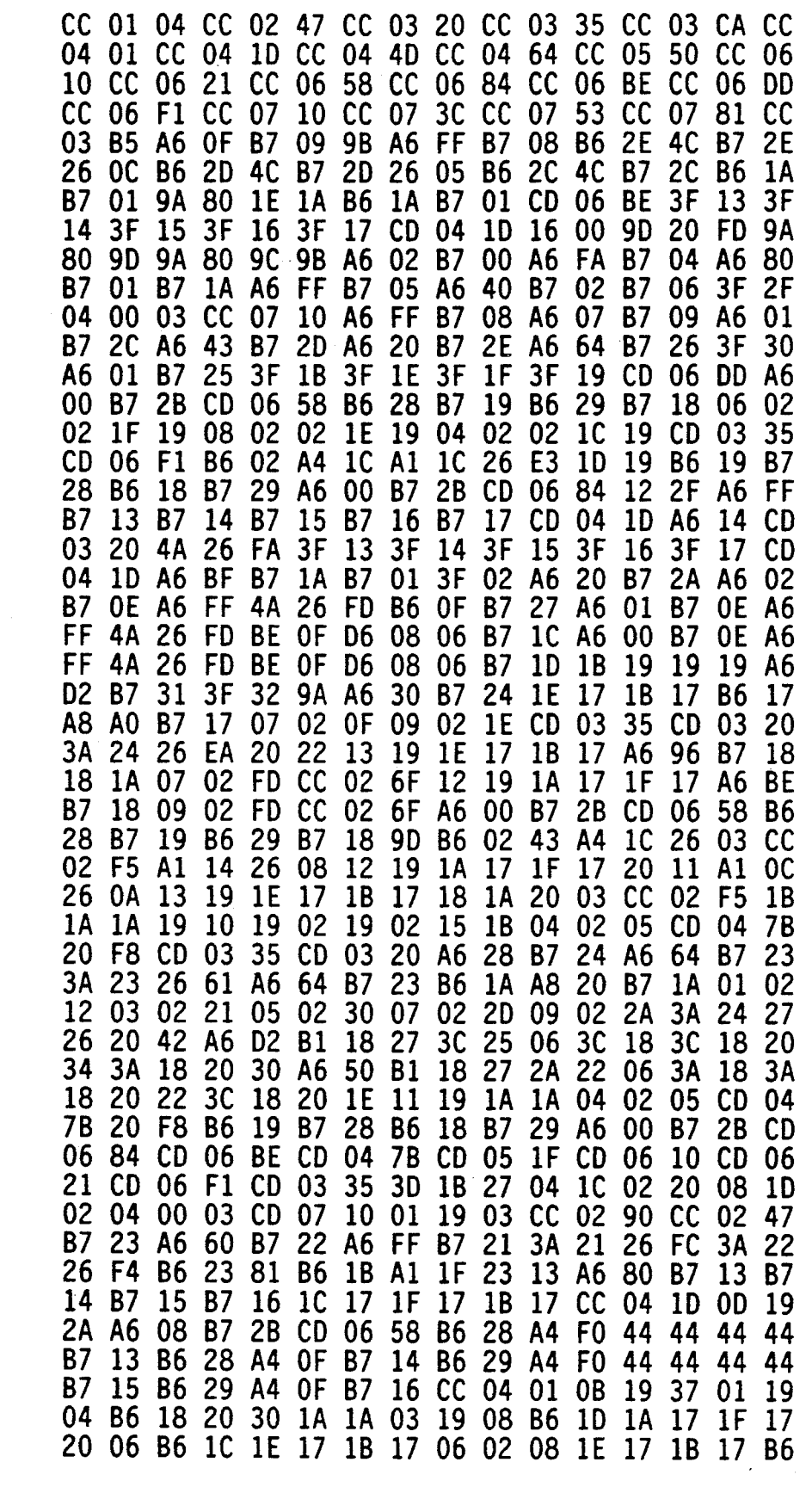
Figure 9B:
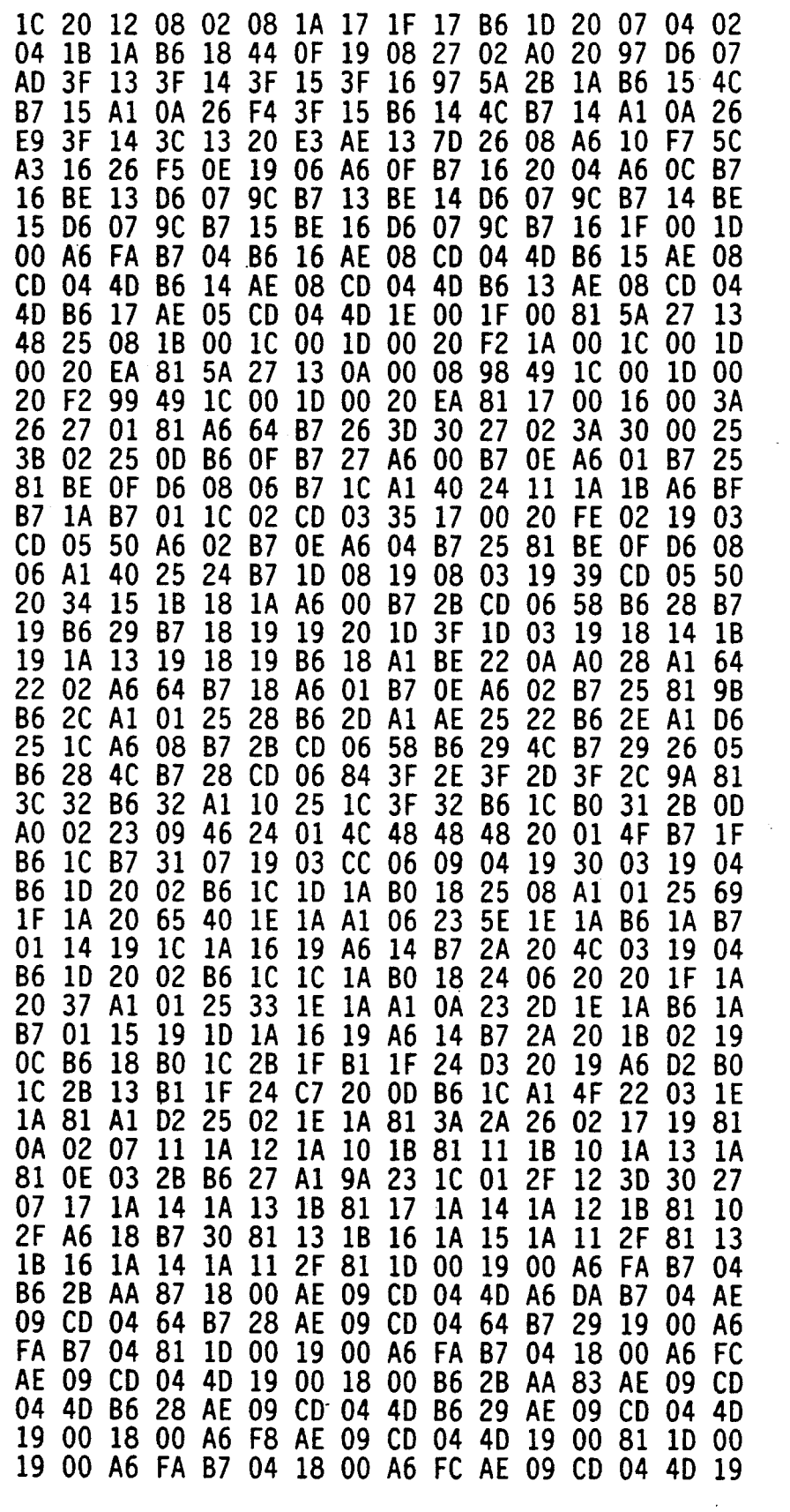
Figure 9C:
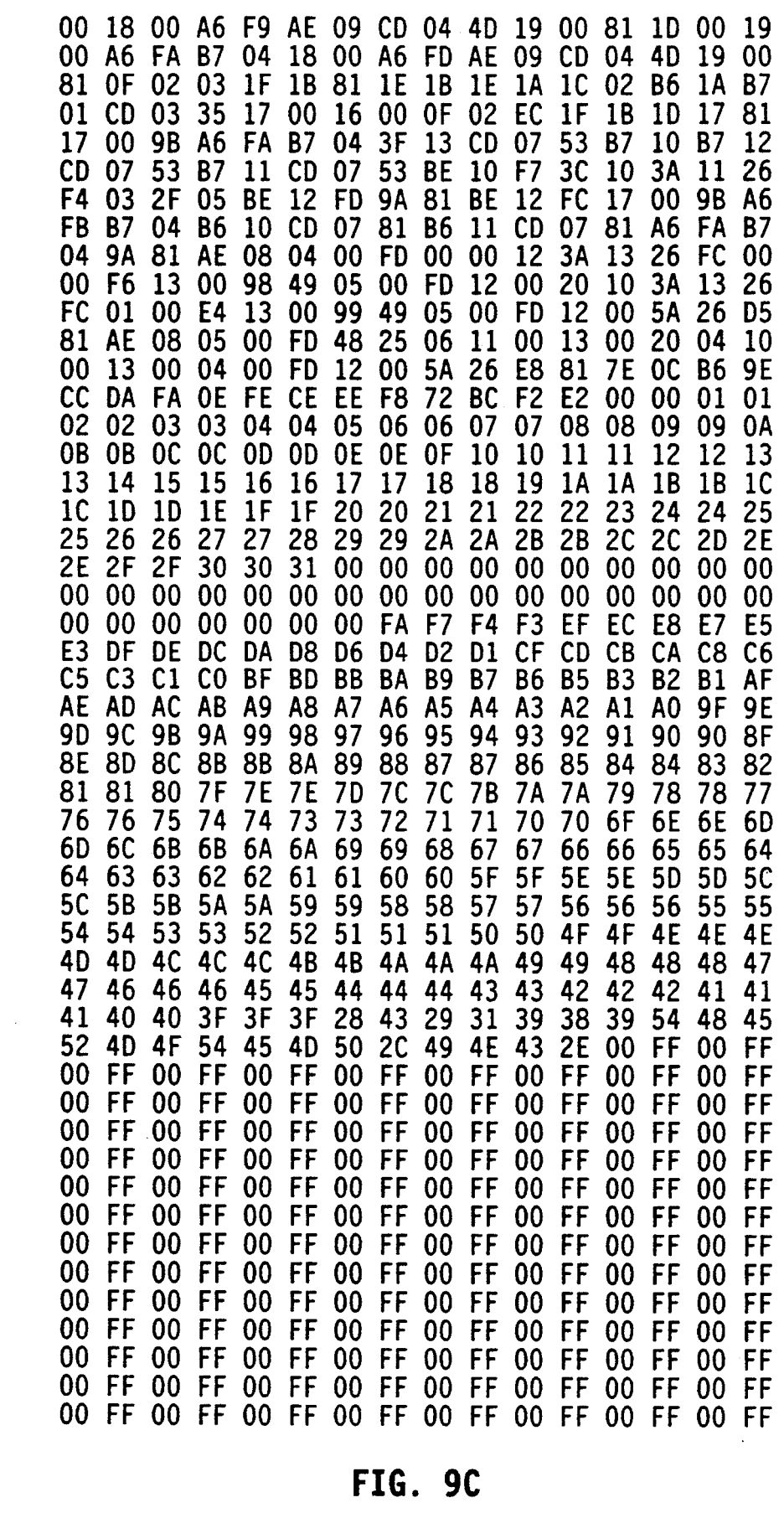
Figure 9D:
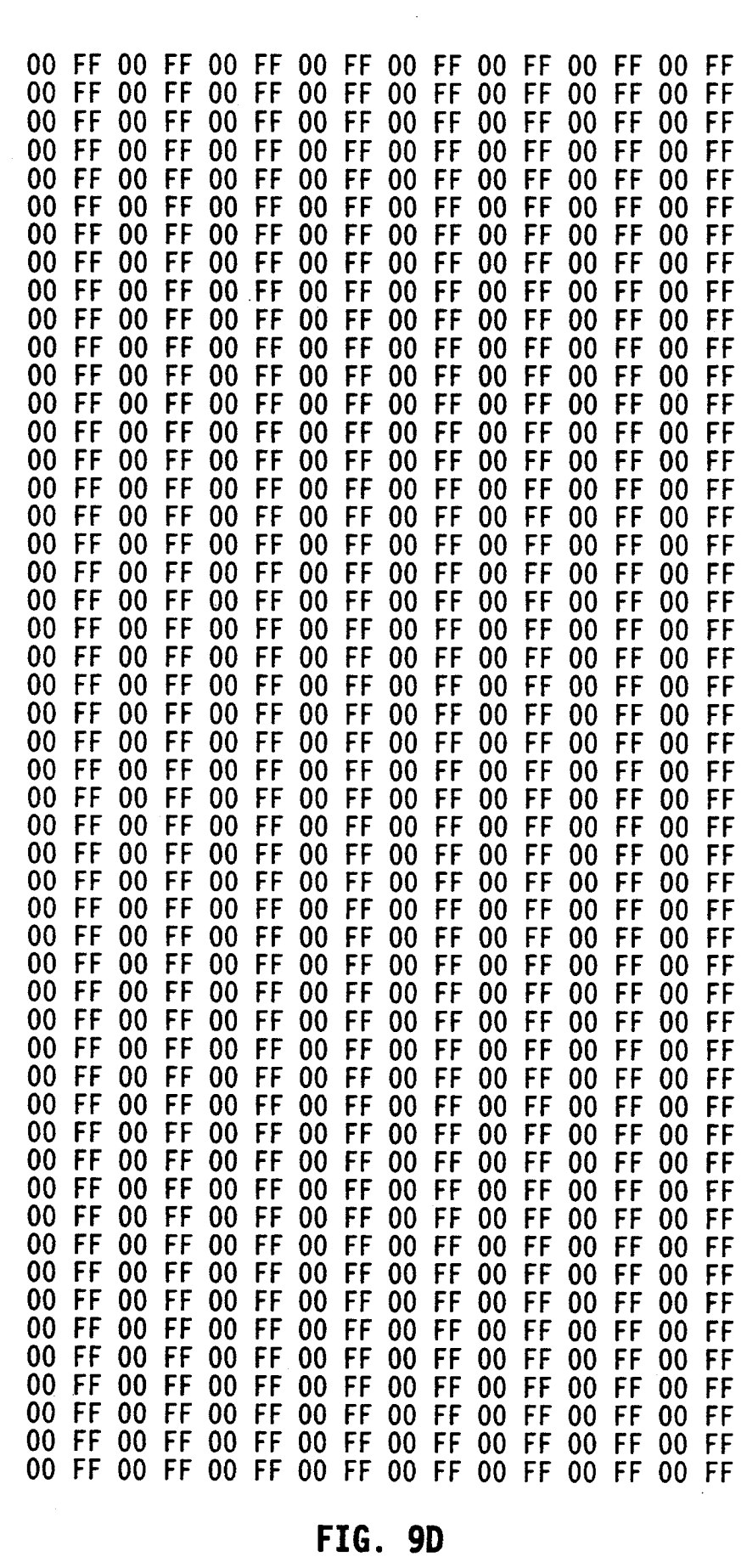
Figure 9E:
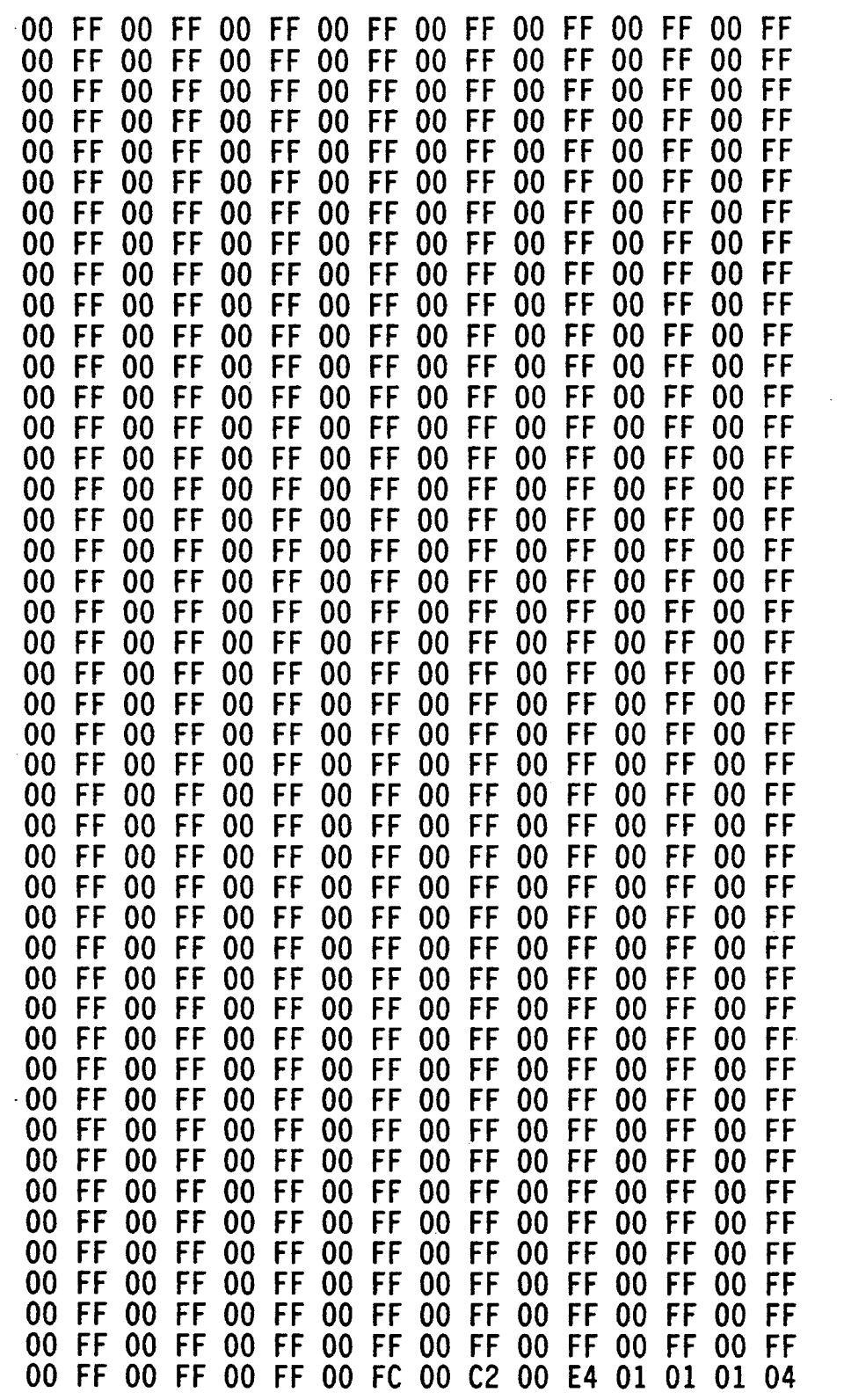

FIGS. 9A through 9E respresent the entire firmware coding program for the fluid flow control system.

Similar reference characters refer to similar parts throughout the several views of the drawings.

DETAILED DESCRIPTION OF THE PREFERRED EMBODIMENT

The present invention relates to a temperature control system comprising a system indicator means, system sensor means and systems control means as described more fully hereinafter for use with a fluid circulating system similar to the temperature control fluid circulating system disclosed in U.S. Pat. No. 4,459,468.

Figure 1:
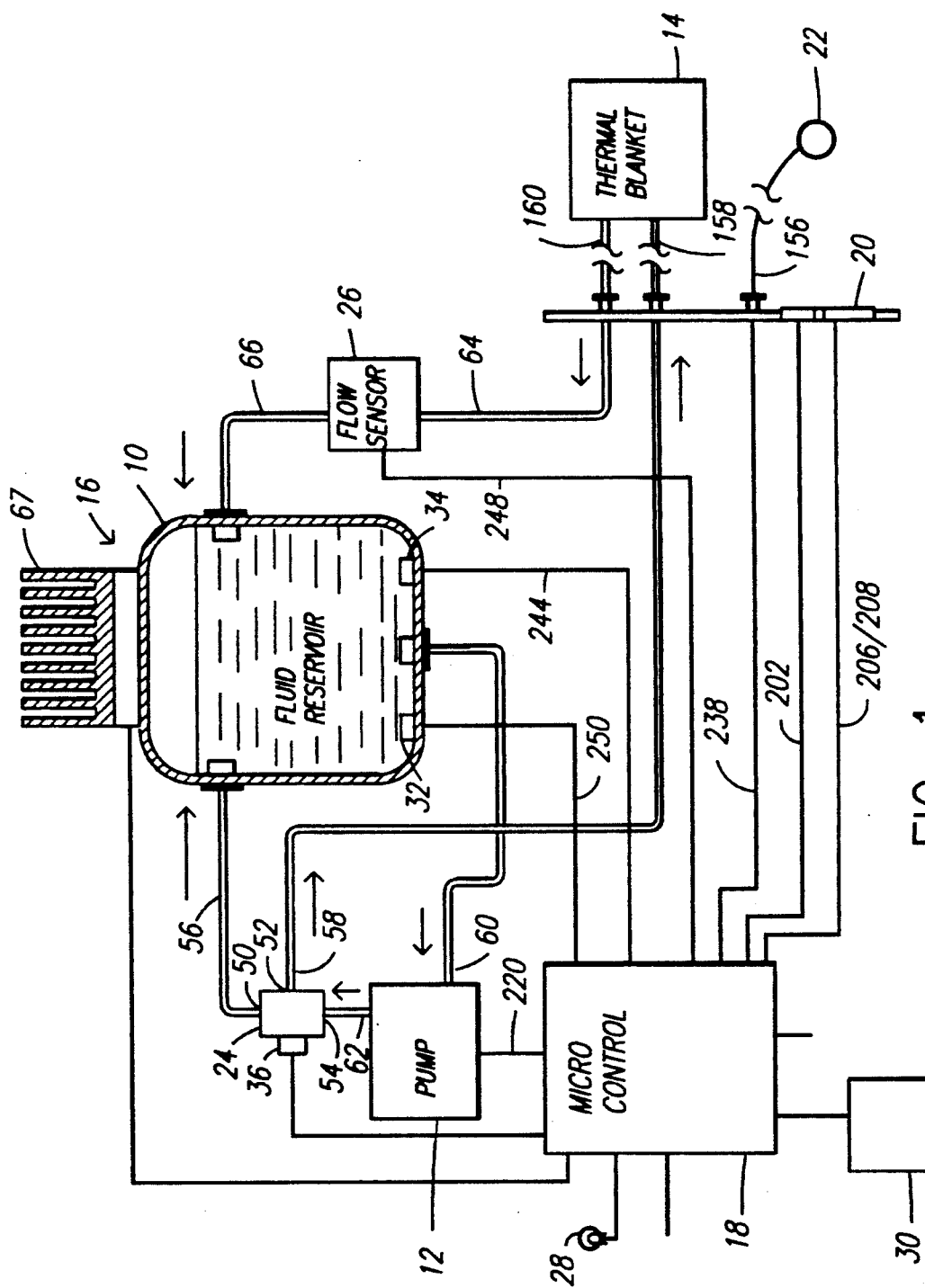
FIG. 1 is a schematic view of a fluid circulating system including the fluid flow control system of the present invention.

As shown in FIG. 1, the fluid circulating system comprises a fluid reservoir 10 coupled to a magnetically coupled centrifugal pump 12 and a thermal blanket or similar remote liquid circulation manifold 14 to selectively circulate fluid to and from the remote liquid circulating manifold 14. The operation of thermal modules 16, disposed in thermal transfer relationship with the fluid reservoir 10, is controlled by a micro control 18 and a display/control panel 20. The fluid circulating system further includes a remote temperature sensor 22 including means to generate a remote temperature signal corresponding to the temperature at the remote site, a fluid flow control device 24 including means to selectively direct the output of the magnetically coupled centrifugal pump 12 to the fluid reservoir 10 or remote liquid circulating manifold 14, fluid flow sensor 26 including means to detect fluid flow and means to generate a fluid flow signal in response thereto, system warning indicator 28 and power supply 30. A fluid level sensor 32 including means to generate a fluid level signal when the fluid level reaches a predetermined minimum level and fluid temperature sensor 34 including means to generate a fluid temperature signal corresponding to the fluid temperature are operatively disposed within the fluid reservoir 10; while a thermostat 36 selectively operable in a first or second state is operatively disposed within the fluid flow control device 24.

As shown in FIG. 1, the fluid flow control device 24 includes a gas outlet, liquid outlet and fluid inlet indicated as 50, 52, and 54 respectively. The gas outlet 50 is coupled to the upper portion of the fluid reservoir 10 by a first fluid conduit 56; while, the liquid outlet 52 is coupled to the inlet side of the thermal blanket 14 through a second fluid conduit 58. The fluid inlet 54 is coupled to the lower portion of the fluid reservoir 10 through the magnetically coupled centrifugal pump 12 by a third and fourth fluid conduit indicated as 60 and 62 respectively. The outlet side of the thermal blanket 14 is coupled to the upper portion of the fluid reservoir 10 through the flow sensor 26 and a fifth and sixth conduit indicated as 64 and 66 respectively.

Figure 2:
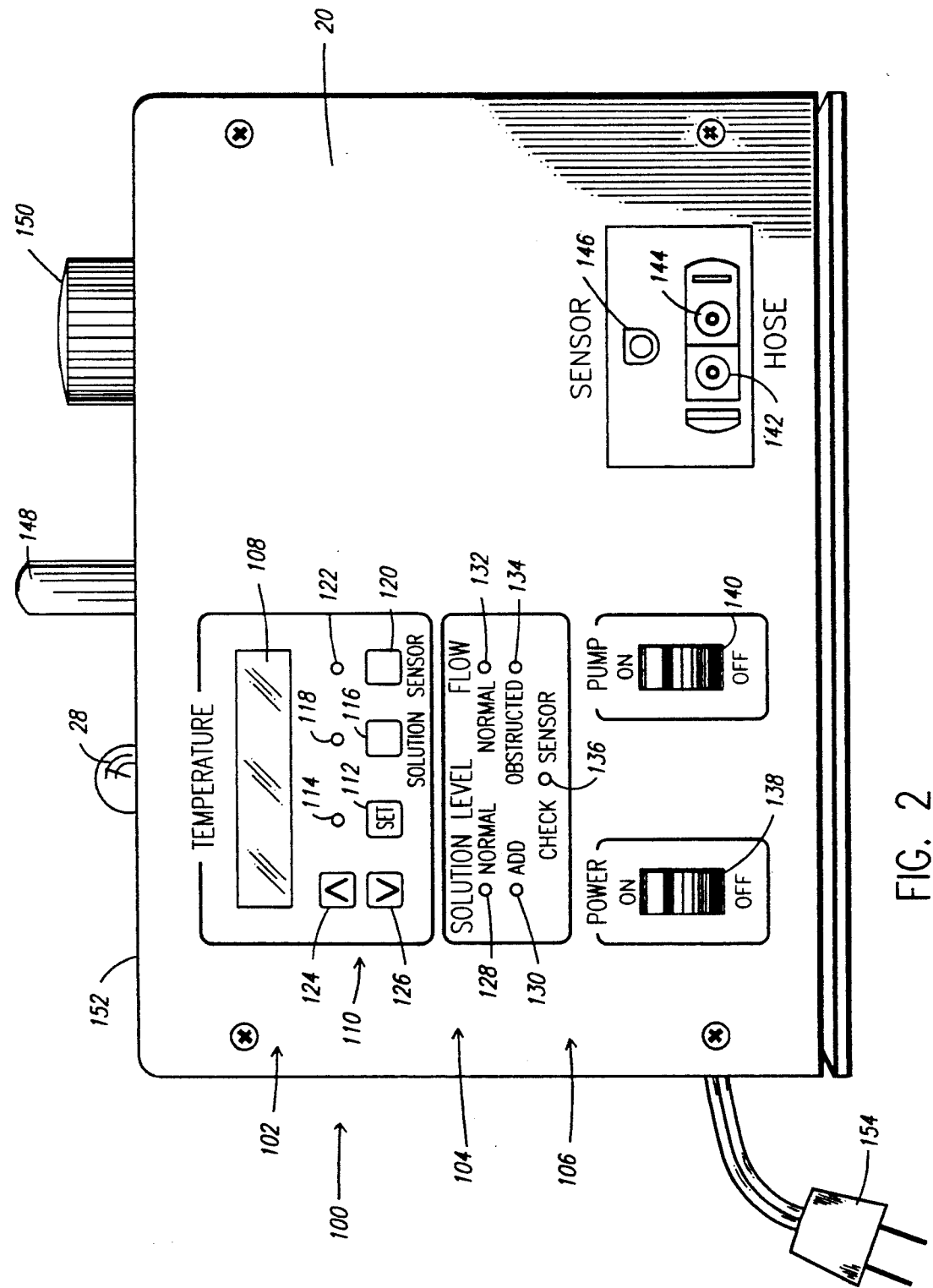
FIG. 2 is a front view of the fluid circulating system cabinet and display/control panel.

As shown in FIG. 2, the display/control panel 20 is mounted on a cabinet generally indicated as 100 that operatively houses or supports the magnetically coupled centrifugal pump 12, thermal modules 16 together with heat sink and fan generally indicated as 67 in FIG. 1, fluid reservoir 10, micro control 18, fluid flow control device 24, flow sensor 26, system warning indicator 28 and power supply 30.

The display/control panel 20 comprises a temperature control section, fluid status section and switch control section generally indicated as 102, 104 and 106 respectively. The temperature control section 102 comprises a four digit LED temperature display 108 and temperature selection control generally indicated as 110 to select a sensor mode or solution mode and set the desired temperature as described more fully hereinafter. When operating in the sensor mode, the temperature sensed by the remote sensor 22 is fed to the micro control 18 and selectively displayed on the four digit LED temperature display 108. When operating in the solution mode, the temperature sensed by the fluid temperature sensor 34 is fed to the micro control 18 and selectively displayed on the four digit LED temperature display 108. The temperature selection control 110 comprises a set key 112 with corresponding set indicator lamp 114, solution key 116 with corresponding solution indicator lamp 118 and sensor key 120 and corresponding sensor indicator 122. The temperature selection control 110 further includes a temperature increase key 124 and temperature decrease key 126. Depression of the set key 112, solution key 116, sensor key 110, temperature increase key 124 and temperature decrease key 126 will generate a corresponding signal. The fluid status section 104 comprises a normal and a low solution level indicator lamp indicated as 128 and 130 respectively, a normal and obstructed flow indicator lamp indicated as 132 and 134 respectively, and a check sensor indicator lamp 136.

The switch control section 106 comprises a two position power on-off switch 138 and two position pump on-off switch 140. The display/control panel 20 further includes a first and second remote liquid circulation manifold connector 142 and 144 together with a remote temperature sensor connector 146. The system warning indicator 28, handle 148 and reservoir fill cap 150 are located on the top wall 152 of the cabinet 100.

The general operation of the fluid flow control system can best be understood with reference to FIGS. 1 and 2. Specifically, the operator connects the fluid flow control system to an external power source (not shown) by an electric connector 154 and fills the fluid reservoir 10. The remote sensor 22 including a conductor 156 and the remote liquid circulation manifold 14 including an inlet and outlet conduit indicated as 158 and 160 respectively are then connected to the remote temperature sensor connector 146, and the first and second remote liquid circulation manifold connectors 142 and 144 respectively.

With the power switch 138 in the ON position, the operating mode and temperature are selected by using the temperature control section 102 as described more fully hereinafter. With the pump switch 140 in the ON position liquid will normally circulate through the fluid circulating system.

As described more fully hereinafter, the present invention integrates a system indicator means to provide a visual indication of the system operating conditions a system sensor means to monitor the system operating conditions and a system control means to control the system operation to implement a plurality of unique features including a power on sequence to control the selection of the operating mode and temperature, a contingent temperature set operation to operate in the solution mode when a remote sensor malfunction condition exists, a fluid flow warning indicator to indicate status of fluid flow through the fluid flow control system and a thermal module control to control the fluid temperature.

Figure 3:
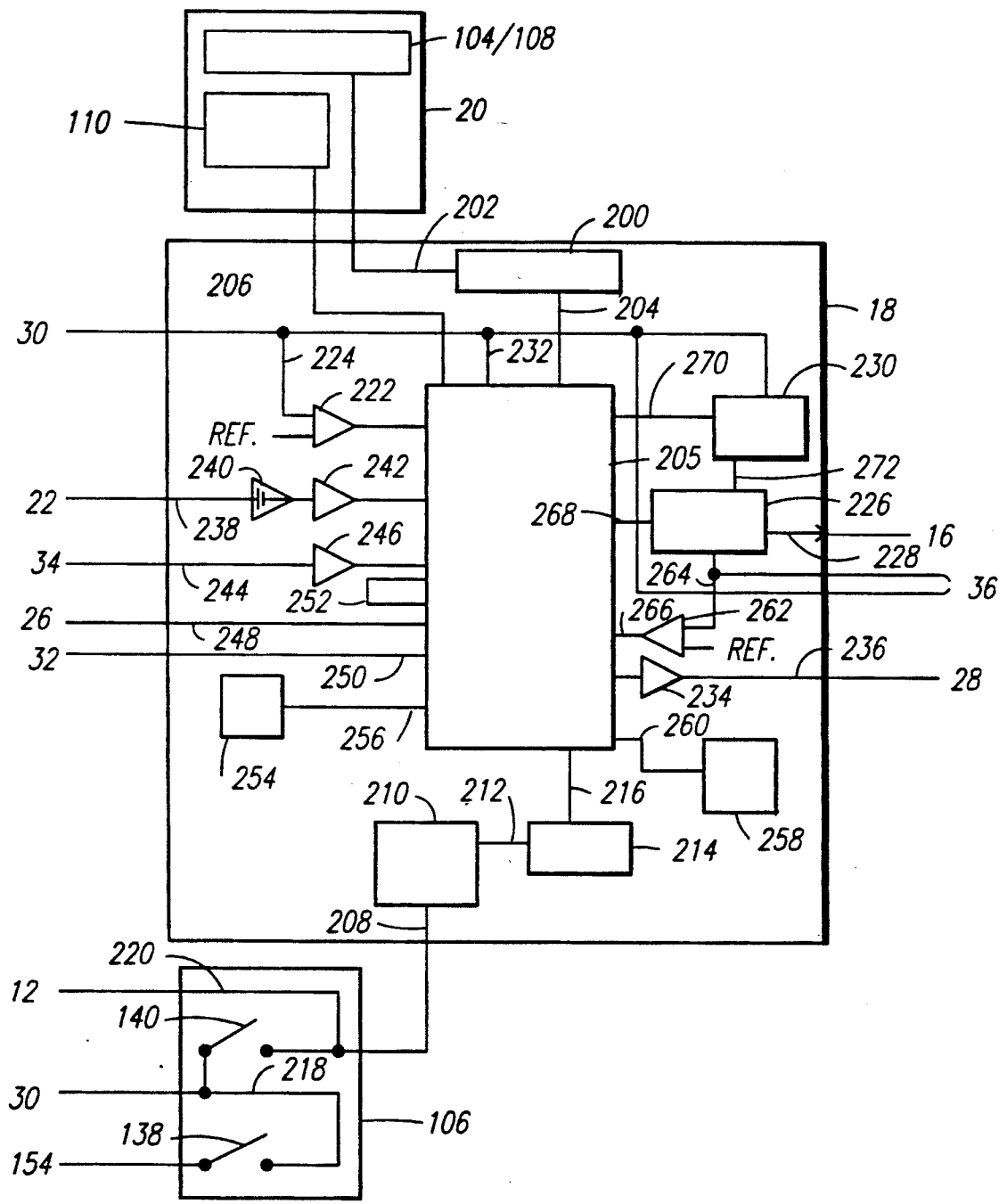
FIG. 3 is a functional block and schematic diagram of the fluid control system.

FIG. 3 is a functional block and schematic diagram of the temperature control system. The indicator lamps of the fluid status section 104 and the four digit LED temperature display 108 are coupled through display driver 200 by conductors 202 and 204. The set key 112, solution key 116, sensor key 120, temperature increase key 124 and temperature decrease key 126 are electrically connected to the microcomputer 205 such as Motorola MC6805R3 through conductor 206. The power control section 106 is electrically connected to the microcomputer 205 through conductor 208, optical isolators 210, conductor 212 filter 214 and conductor 216. Electric connector 154 is electrically coupled directly to the two position power on-off switch 138 which is, in turn, connected to both the two position pump on-off switch 140 and the power supply 30 by conductor 218. The two position pump on-off switch 140 is coupled to the magnetically coupled centrifugal pump 12 through conductor 220 and to the optical isolator 210 through conductor 208. The output of the DC power supply 30 is electrically coupled to the a comparator 222 by conductor 224. The thermal modules 16 are electrically connected to control relay or first thermal module control switch 226 by conductor 228. The control relay 226 is, in turn, electrically connected to the DC power supply 30 through a transistor or second thermal module control switch 230 and thermostat 36. In addition, the DC power supply 30 is coupled directly to the microcomputer 205 by conductor 232 to provide other system power requirements. System warning indicator 28 is coupled through amplifier 234 and conductor 236 to the microcomputer 205. The remote temperature sensor 22 is electrically connected to the microcomputer 205 by a conductor 238 through an isolation amplifier 240 and amplifier 242; while, the fluid temperature sensor 34 is electrically connected to the microcomputer 205 by conductor 244 through amplifier 246. The flow sensor 26 is electrically connected to the microcomputer 205 through conductor 248; while, the fluid level sensor 32 is electrically connected to the microcomputer 205 by conductor 250. A system clock 252 is coupled to the microcomputer 205 to provide the necessary timing of the temperature control system. A microcomputer operations monitor 254 capable of generating a reset signal when invalid microcomputer operation is detected is electrically connected to the microcomputer 205 by conductor 260. The non-volatile random access memory 258 is electrically connected to the microcomputer 205 by conductor 260. The non-volatile random access memory 258 stores the manually selected or default temperature set point, operating mode and elapsed operating time. A comparator 262 is electrically connected between the return DC power from the thermostat 36 by conductor 264 and the microcomputer 205 by conductor 266.

The microcomputer 205 includes power on logic circuitry to sequentially generate a plurality of power on signals.

Figure 4:
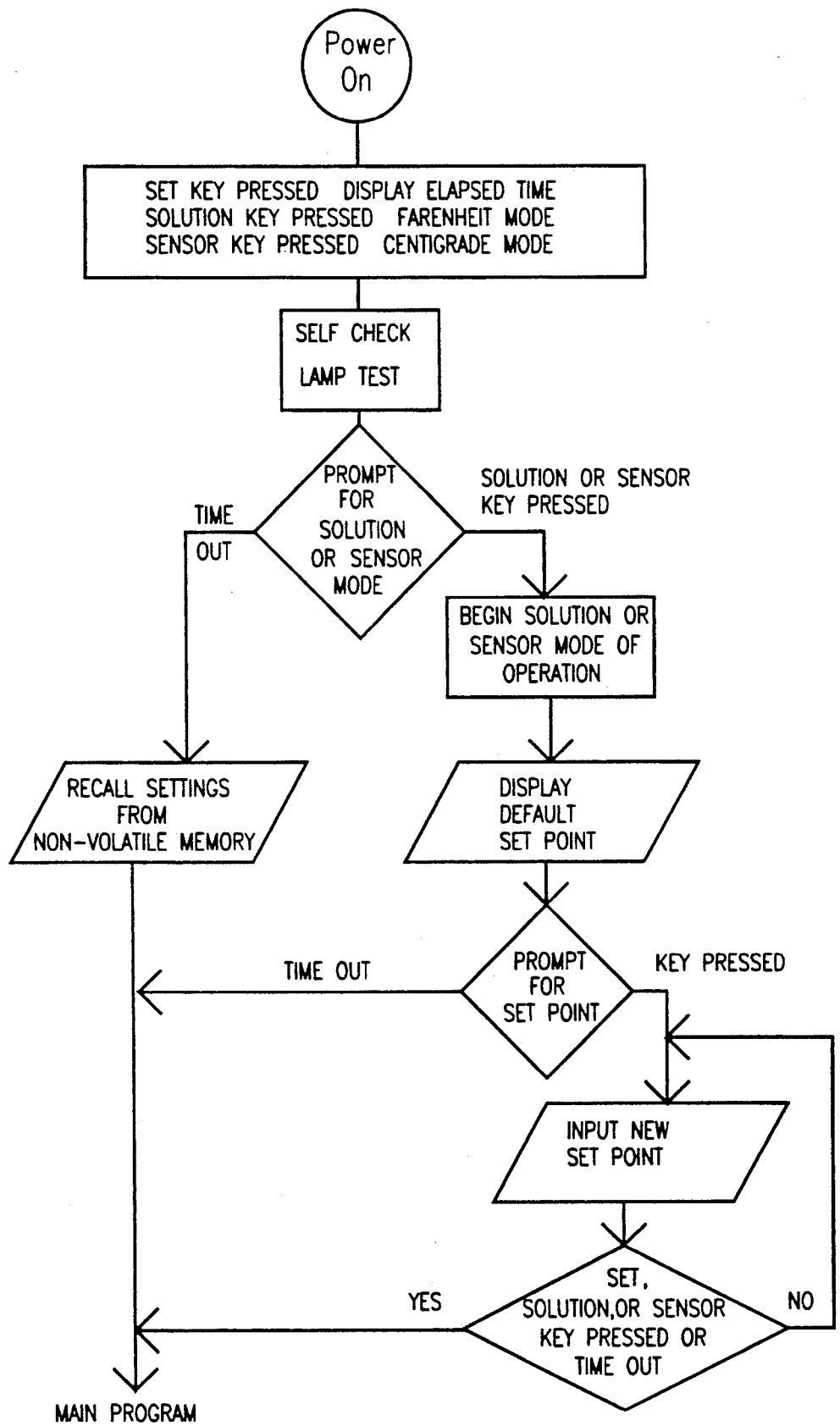
FIG. 4 is a flow chart of the power on sequence.
Figure 5:
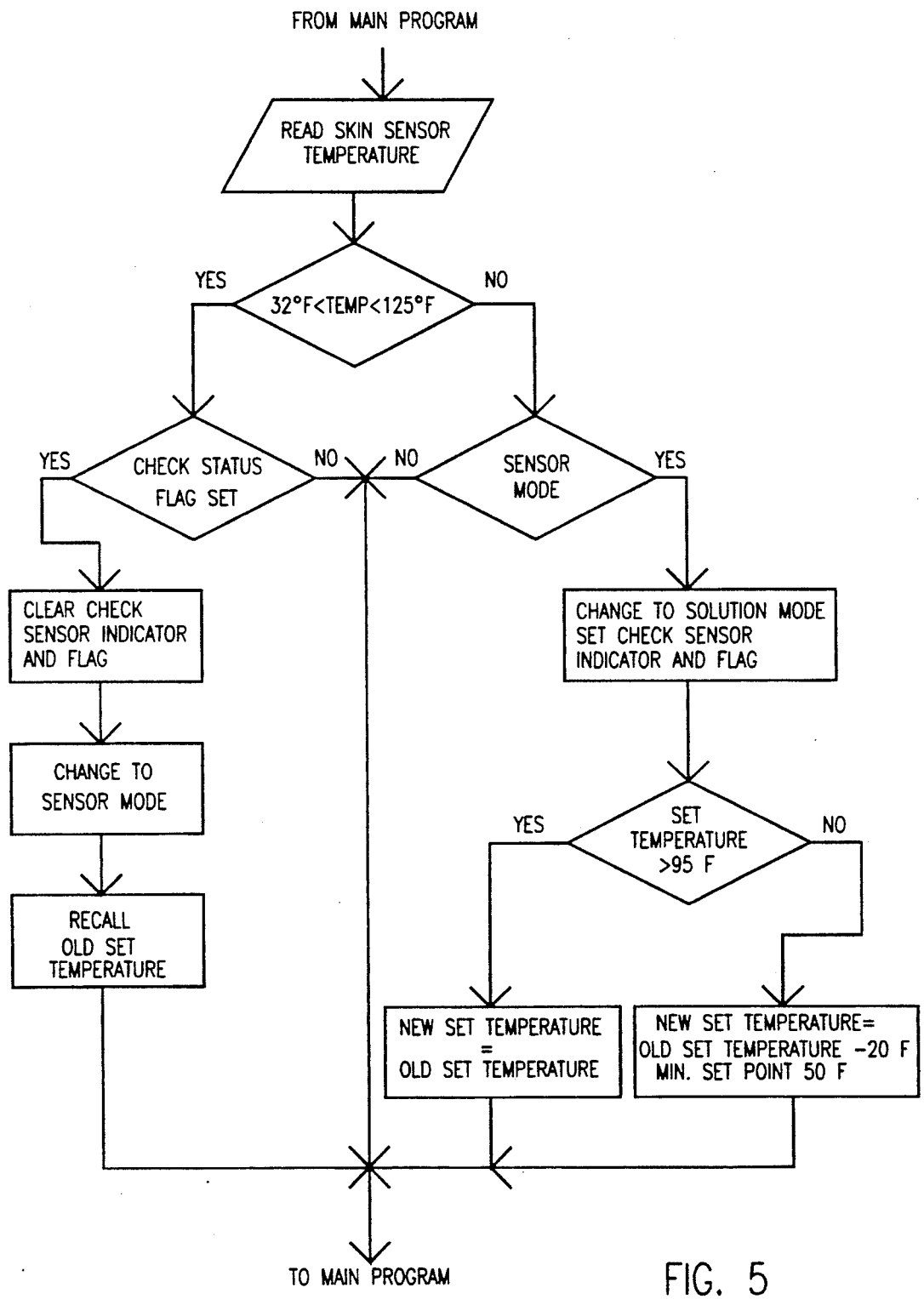
FIG. 5 is a flow chart of the contingent temperature.

The operation of the power on logic circuitry can best be understood with reference to FIG. 4. Specifically, if the set key 112, solution key 116 or sensor key 120 is depressed when the power switch 138 is in ON position, the power on logic circuitry will generate signals to display 108 the contents on the non-volatile random access memory elapsed operating time memory location, a signal to illuminate the character "F" on display 108 and store the Fahrenheit flag in the non-volatile random access memory mode resiter, a signal to illuminate the character "C" on display 108 and store the Centigrade flag in the non-volatile random access memory mode register.

After a series of self check lamp tests, solution indicator 114 and sensor indicator 122 are alternatively illuminated and solution key 116 and sensor key 120 outputs on conductor 206 are checked for actuation for a predetermined period of time such as 10 seconds. If neither keys were actuated, then the memory contents of non-volatile random access memory 258 are stored in the microcomputer 205 registers for set point and mode, the display 108 will illuminate the respective sensor temperature and solution indicator 118 or sensor indicator 122. If actuation of solution or sensor key 116 and 118 respectively occurs within the time, the appropriate mode will be stored in the microcomputer 205. Next the display 108 illuminates with a first predetermined set point such as 75 degrees Fahrenheit for solution mode or a predetermined set point such as 95 degrees Fahrenheit for sensor mode and flashes the set indicator lamp 114 and checks the keys 110 for actuation for a predetermined period of time, such as 10 seconds. If any of the keys 110 is not actuated within time, the default set point and mode area stored in the microcomputer 205 and in the non-volatile random access memory 258. If a temperature increase key 124 or temperature decrease key 126 is actuated, the set point register in the microcomputer 205 is incremented or decremented within limits of 105 and 40 degrees Fahrenheit and the current contents of the set point register is illuminated on the display 108. If any one of the keys set 112, solution 116 or sensor 120 is actuated, the current set point and mode are stored in microcomputer 205 and non-volatile random access memory 258. The display 108 will illuminate the respective sensor temperature and solution indicator 118 or sensor indicator 122.

After the logical sequence is completed, microcomputer 205 begins the repetative sequence of its operation.

The micro control 18 further includes alternate sensor mode logic circuitry to change the mode of the operation from the sensor mode to the solution mode when temperature signal from the remote sensor 22 is not within a predetermined temperature range such as between 32 degrees Fahrenheit and 125 degrees Fahrenheit. Specifically, the sequence is entered from the main temperature control sequence. First it reads the skin sensor temperature. The temperature is compared within a predetermined temperature range such as greater than 32 degrees Fahrenheit but less than 125 degrees Fahrenheit. If the input temperature is not within this predetermined temperature range, the mode of operation is then checked. If the system is not in the sensor mode, then continue the main temperature control sequence. If the system is in the sensor mode then the system changes to the solution mode. It sets the check sensor indicator 136 on the front panel and sets a flag in the status register in microcomputer 205. The flag set in the status register indicates that the mode has been changed to solution with contingent operation. Next, the set point temperature is compared with 95 degrees Fahrenheit, if the set point is above 95 degrees, the new set point temperature equals the sensor mode set point temperature, if the set point is less than or equal to 95 degrees Fahrenheit, then the new set point is sensor mode set point minus 20 degrees Fahrenheit with a minimum set point of 50 degrees Fahrenheit and then continue the main temperature control sequence. From the initial comparison of the input temperature of between 32 and 125 degrees, if the resulted input temperature is between these bounds, then the status register will be checked to determine if the status flag is set. If the flag is not set then continue the main temperature control sequence. If the flag is set and the check sensor indicator lamp 136 is ON, then turn OFF the check sensor indicator lamp 136 and clear the status flag. Change the mode to sensor operation then recall the previous set temperature from the non-volatile random access memory 258 and continue the main temperature control sequence.

The micro control 18 includes a fluid flow sensor indicator control means to selectively control the illumination of the normal flow indicator lamp 132, obstructed flow indicator lamp 134 and system warning indicator 28.

Figure 6:
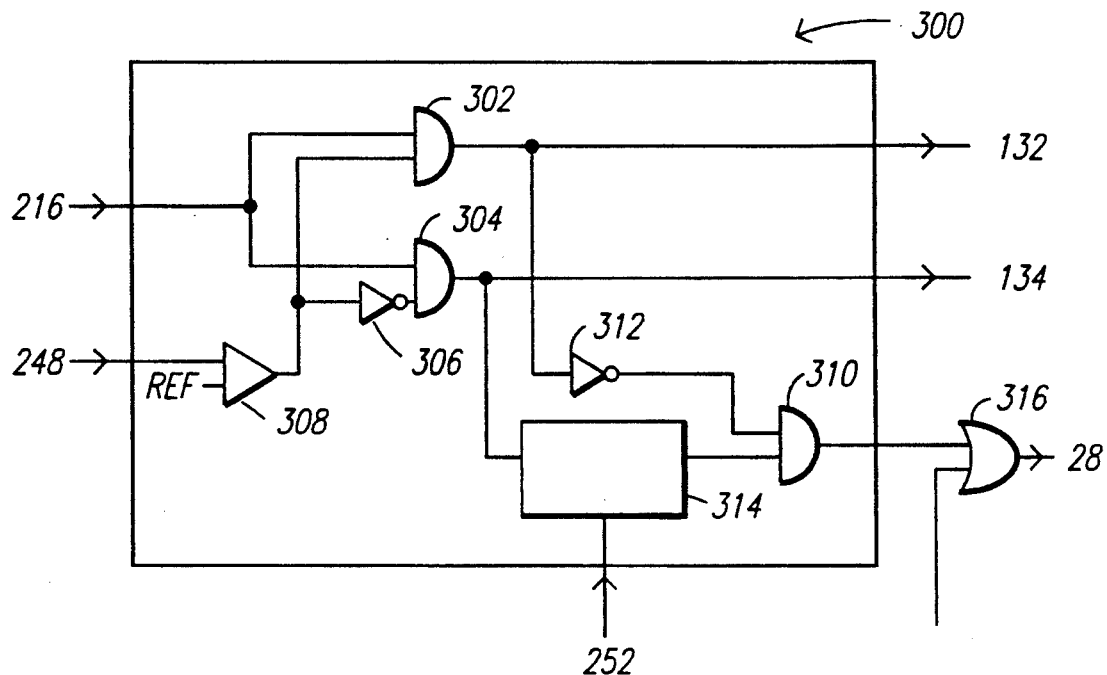
FIG. 6 is a schematic diagram of the obstruction warning.

FIG. 6 is a schematic diagram of the fluid flow indicator logic circuitry generally indicated as 300 to receive signals from the magnetically coupled centrifugal pump 12 and the fluid flow sensor 26 and selectively generate a first, second or third fluid flow signal in response thereto. Specifically, input signals from the magnetically coupled centrifugal pump 12 is ON are fed to AND gate 302 and AND gate 304. A comparator 308 receives input signals from the flow sensor 26 through conductor 248 along with a reference signal. The output of the comparator 308 is coupled to AND gate 302 and AND gate 304 through an invertor 306. The output of AND gate 302 is coupled to the normal flow indicator lamp 132 and to an AND gate 310 through an invertor 312; while, the output of AND gate 304 is coupled to the obstruction flow indicator lamp 134 and delay circuitry input 314. A timing signal from the clock 252 is also fed to the delay circuitry 314. The output of the delay circuitry 314 is fed to the AND gate 310. The AND gate 310 is then electrically connected to the system warning indicator 28 through OR gate 316. Additional warning conditions are also fed to the system warning indicator 28 through OR gate 316. When the magnetically coupled centrifugal pump 12 is ON and the flow indication signal is received from the fluid flow sensor 26, the fluid flow indicator logic circuitry 300 will generate a first signal illuminating the normal flow indicator lamp 132. When the magnetically coupled centrifugal pump 12 is ON and no flow indication signal is received from the flow sensor 26, the fluid flow indicator logic circuitry 300 will generate a second signal illuminating the obstructed flow indicator lamp 134. When the magnetically coupled centrifugal pump 12 is ON and no flow indication signal received from the fluid flow sensor 26 within a predetermined period of time such as 10 seconds, the fluid flow indicator logic circuitry 300 will generate a third signal to illuminate the system warning indicator 28.

The micro control 18 includes a thermal module temperature control means comprising a first order temperature control including heat and cool logic circuitry similar to that disclosed in U.S. Pat. No. 4,459,468, a temperature rate change control generally indicated as 400 in FIG. 7, a first thermal module control switch 226, second thermal module control switch 230 and thermostat 36. The first order temperature control including the heat and cool logic circuitry compares the measured temperature, either the sensor temperature when in the sensor mode or the solution temperature when in the solution mode, with the set point selected on the display/control panel 20. If selected temperature is greater than the sensed temperature by a first predetermined amount such as 5 degrees Fahrenheit, the first order temperature control generates "heat" signal while, when the sensed temperature is less than the selected temperature by the first predetermined amount the first order temperature control generates a "cool" signal. These "cool" and "heat" signals are fed to the first thermal module control switch 226 through conductor 268. The first order temperature control generates an "active" signal when the selected remote sensor 22 or fluid temperature sensor solution 34 temperature input is less than the set point plus a second predetermined amount such as 2 degrees Fahrenheit for heat mode or an "active" signal when the selected input temperature is greater than the set point minus the second predetermined amount for the cool mode, the "active" signal, when present, is combined with the output of the temperature rate change control 400 in AND gate 416. The combined signal is fed to the second thermal module control switch 230 through conductor 270.

The thermostat 36 includes means to generate an enable signal when the temperature of the fluid is less than a predetermined value such as 110 degrees fed to the first thermal module control switch 226.

Figure 7:
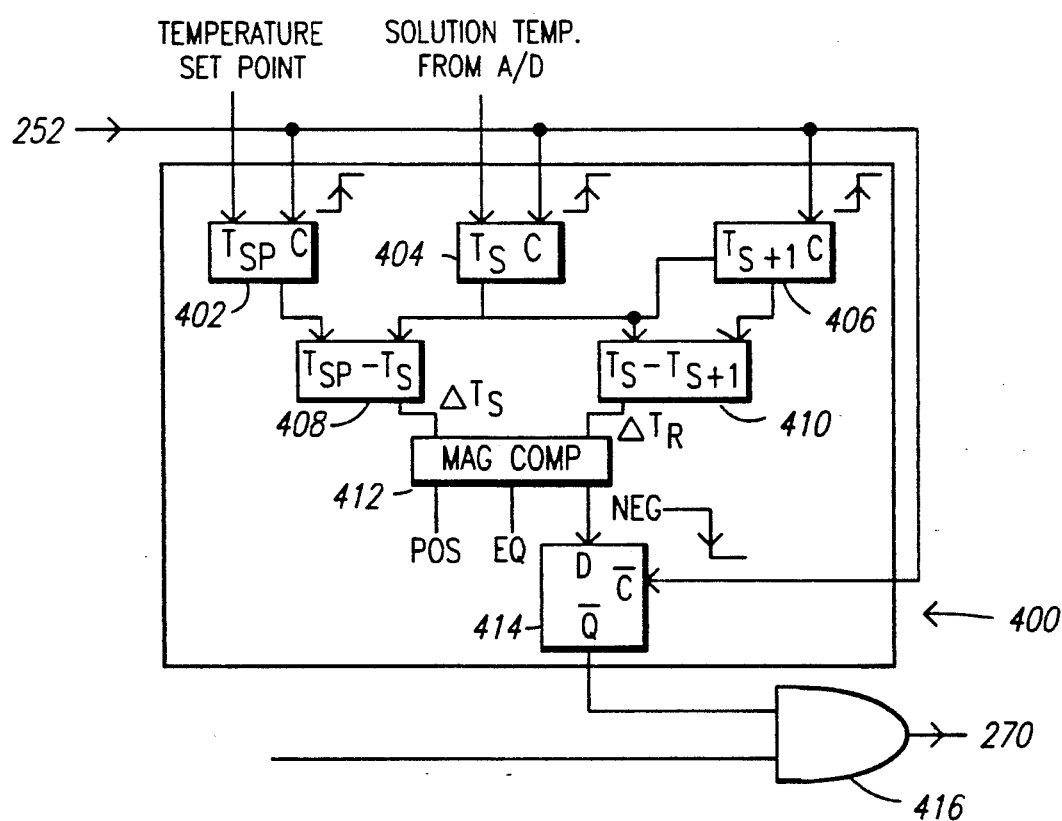
FIG. 7 is a schematic diagram of the temperature control.
Figure 8A:
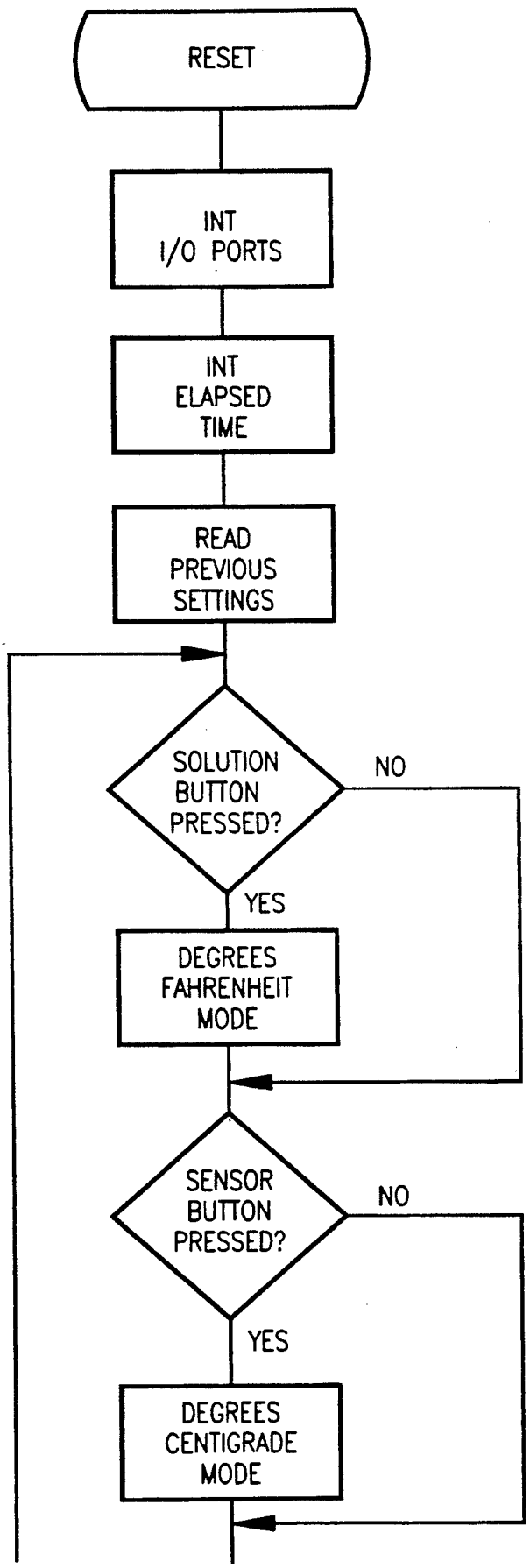
FIGS. 8A through 8J depict the complete flow chart of the fluid flow control system.
Figure 8B:
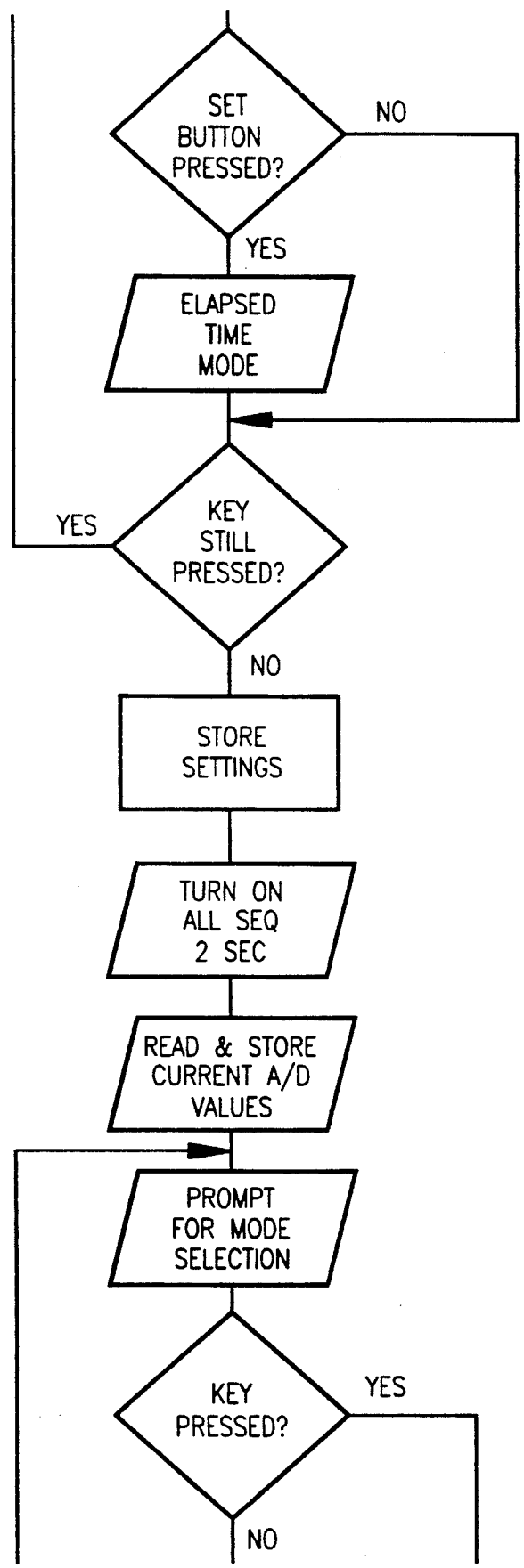
Figure 8C:
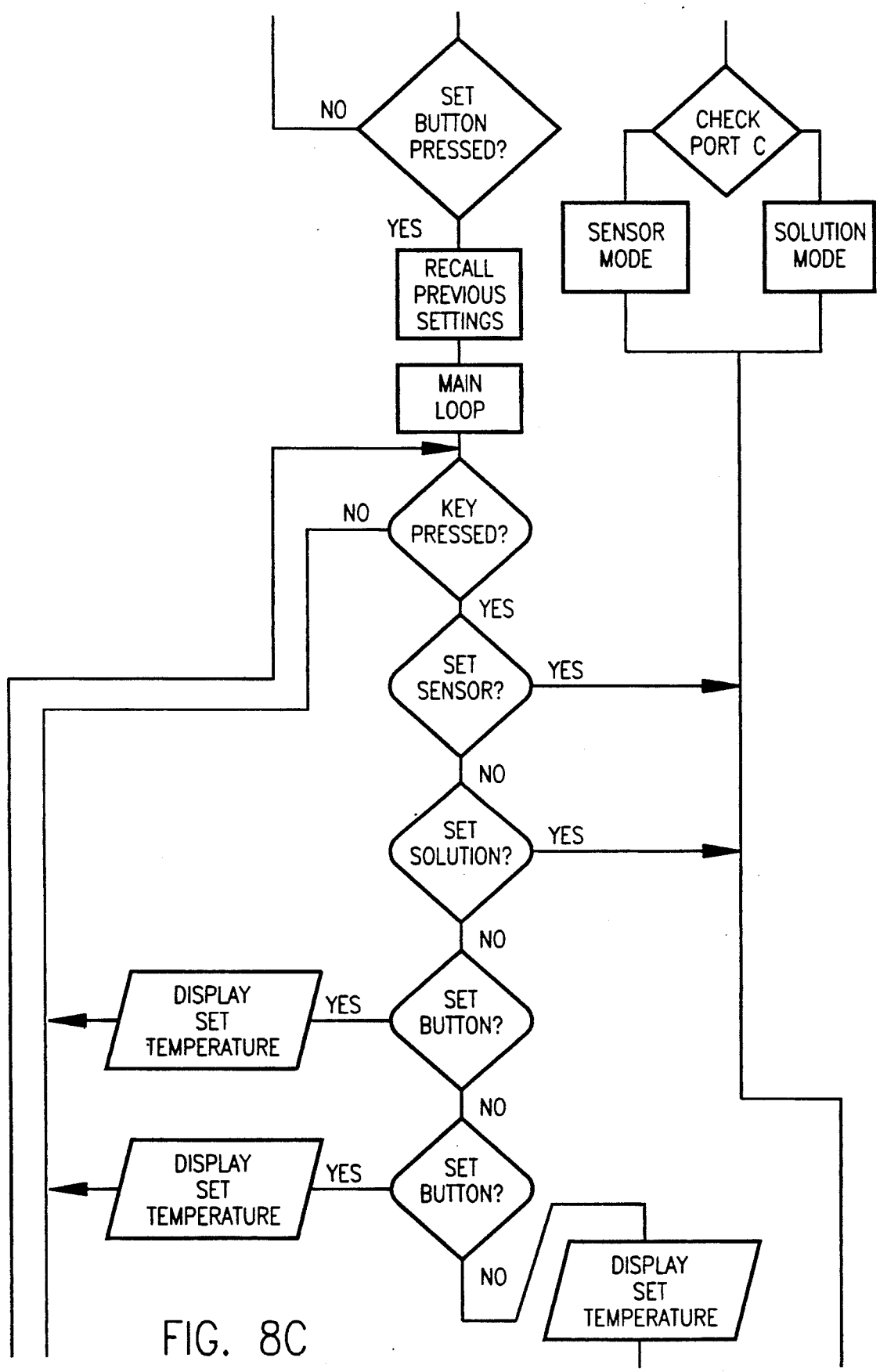
Figure 8D:
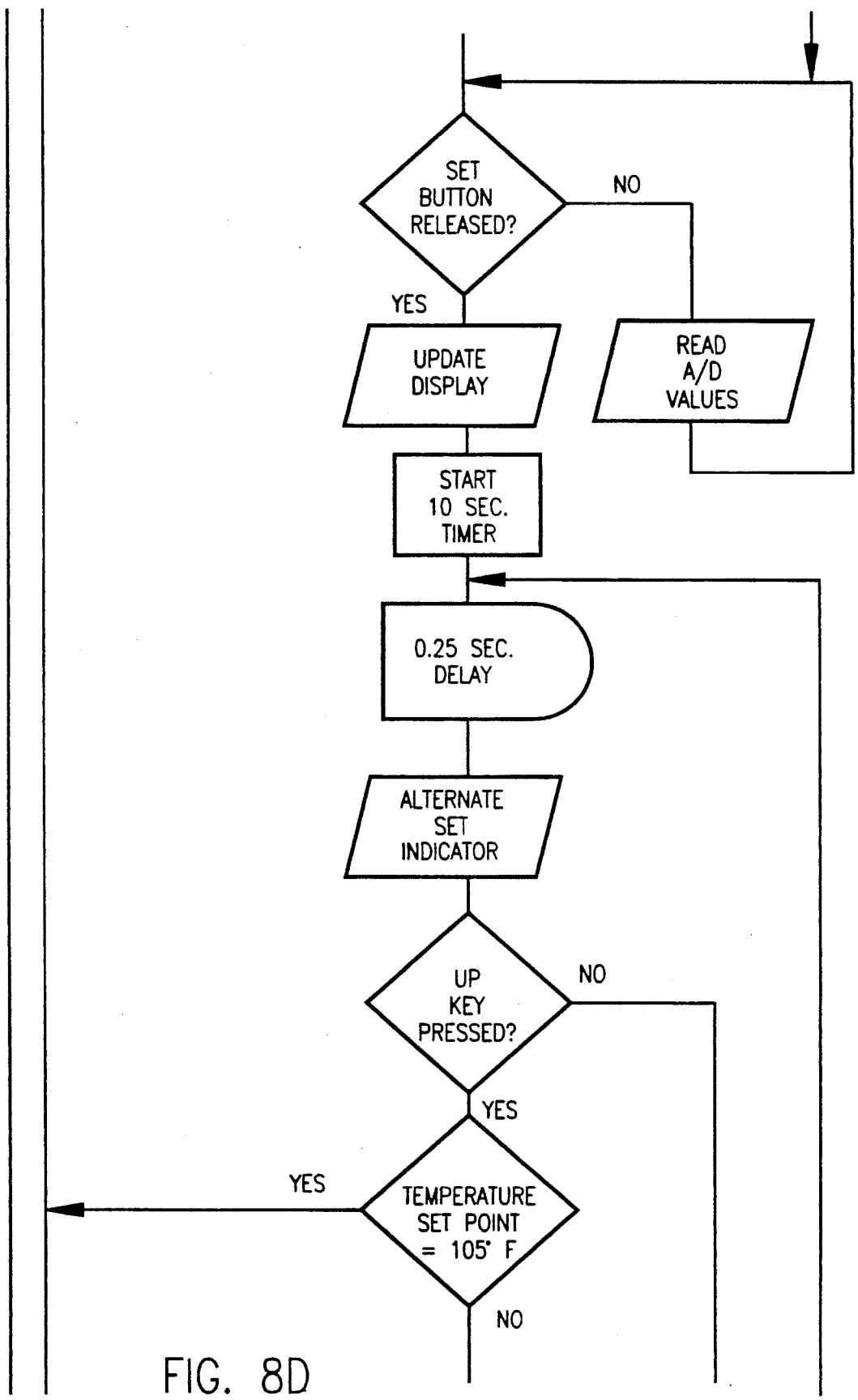
Figure 8E:
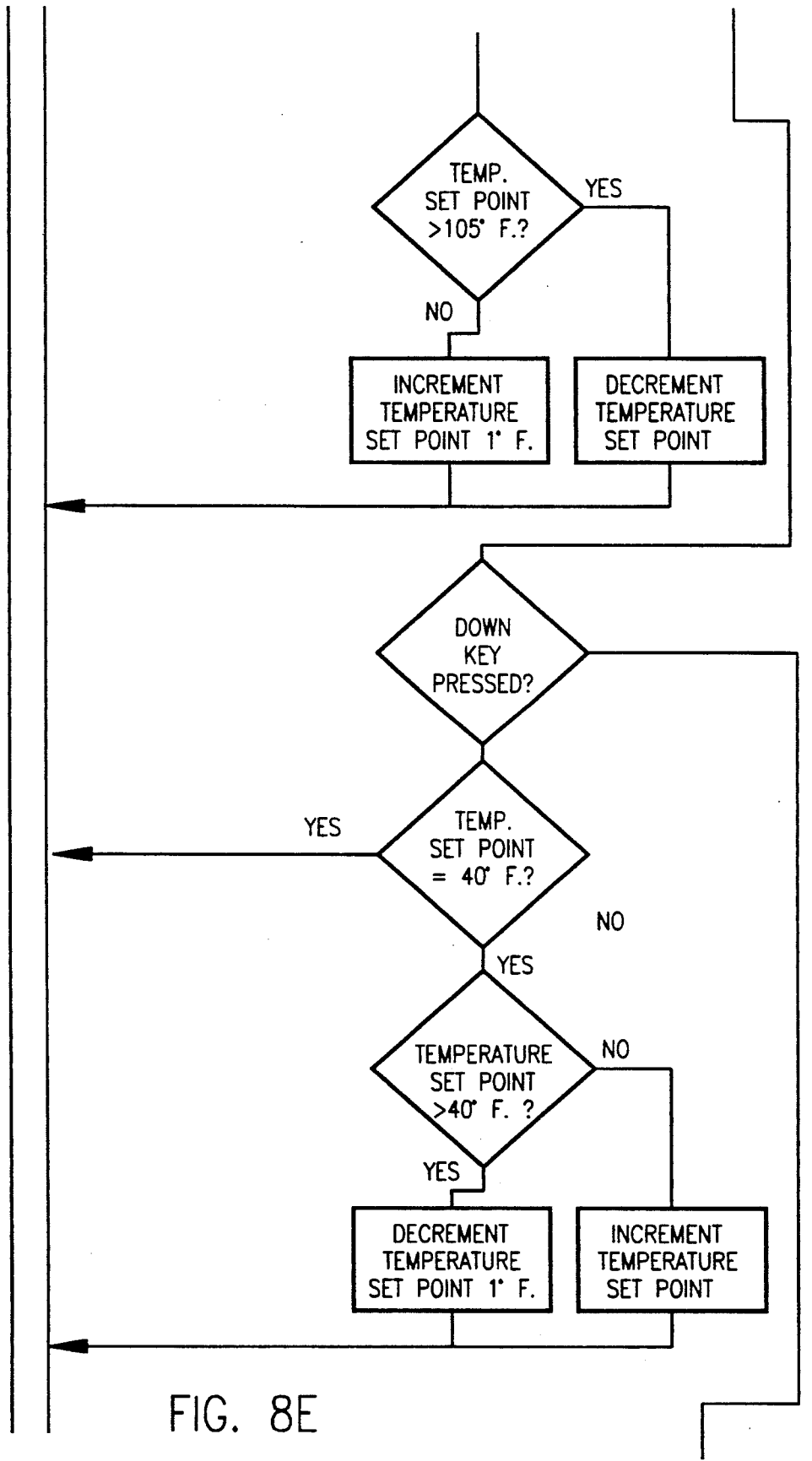
Figure 8F:
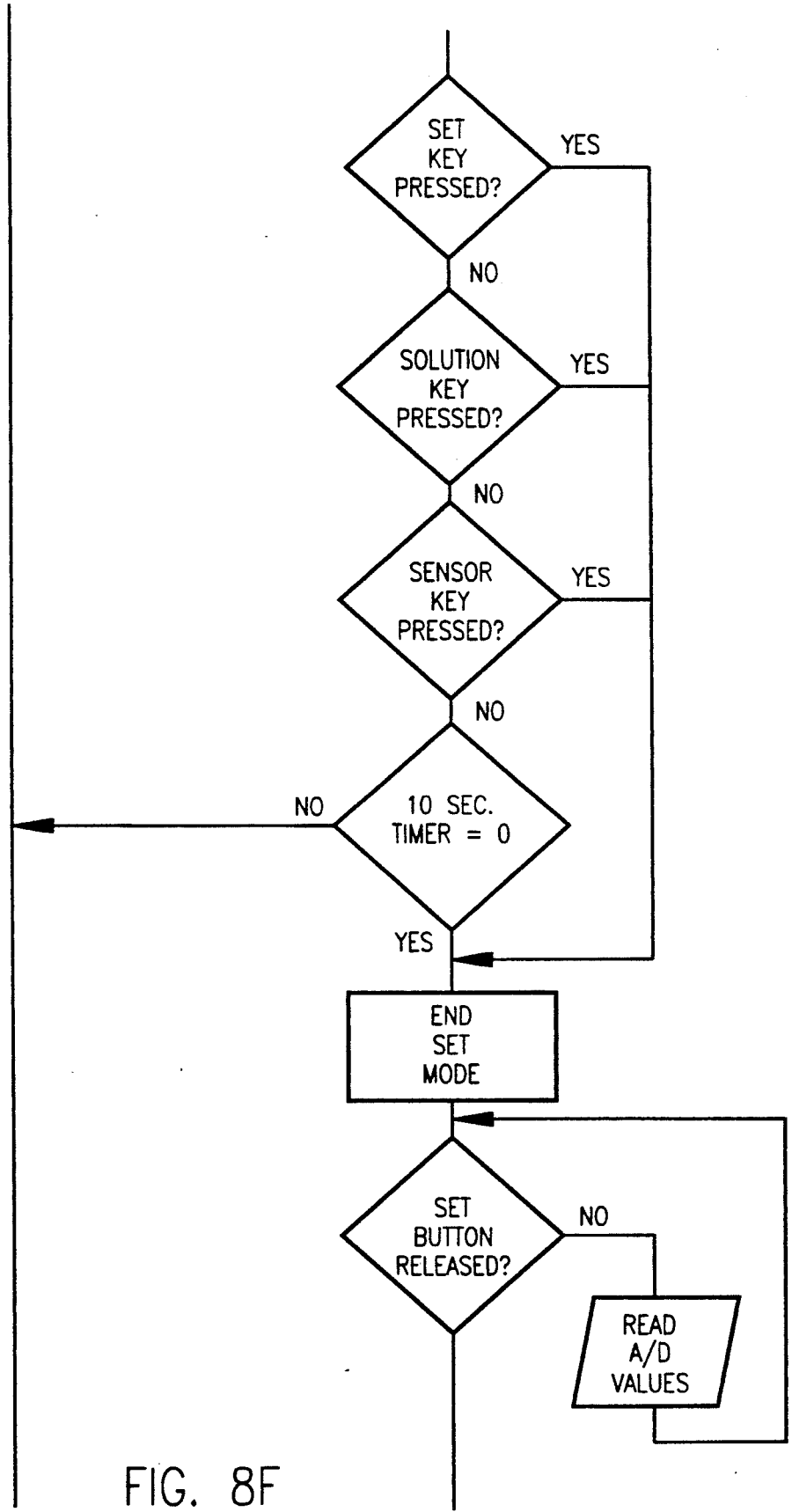
Figure 8G:
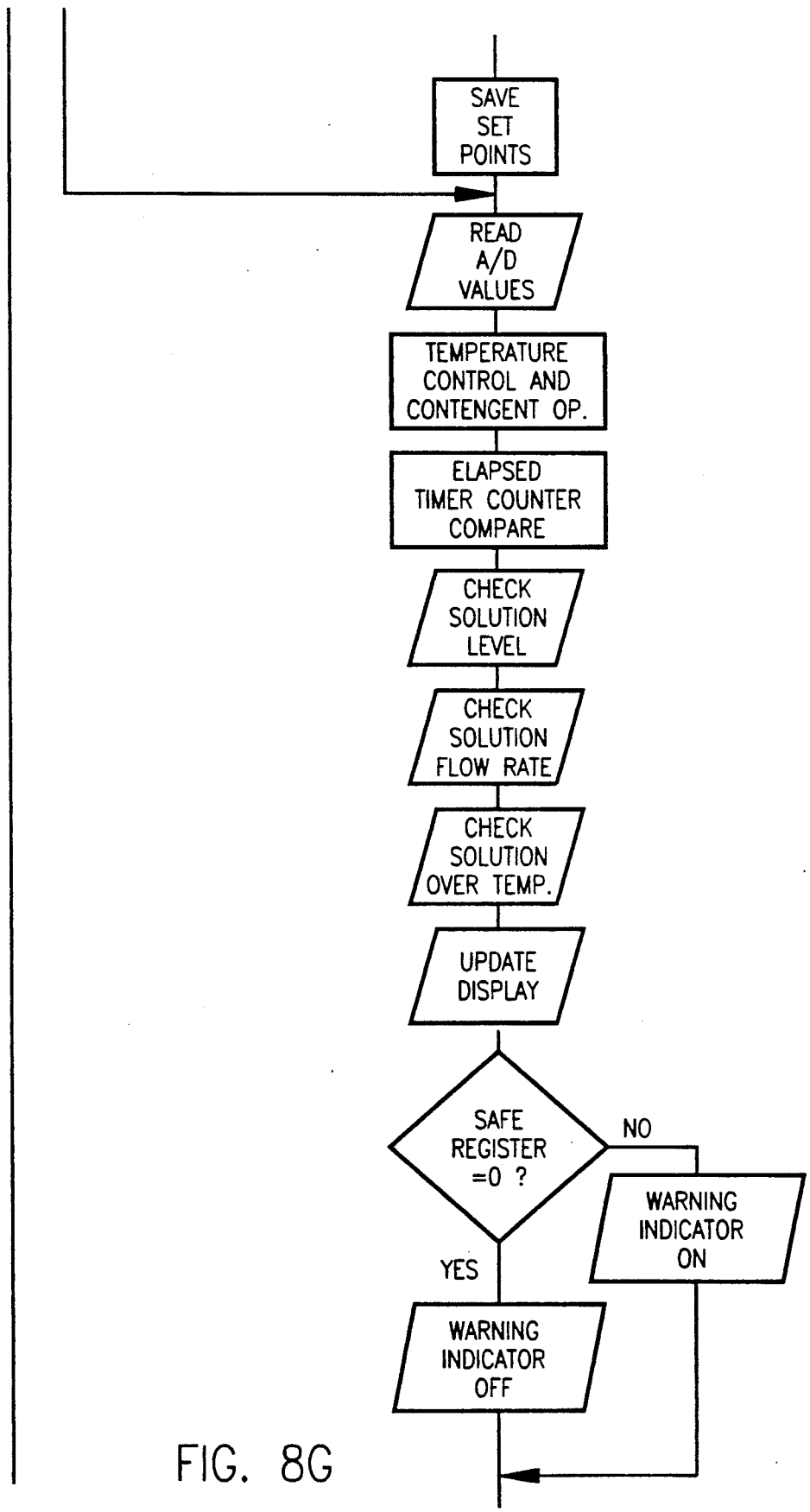
Figure 8H:
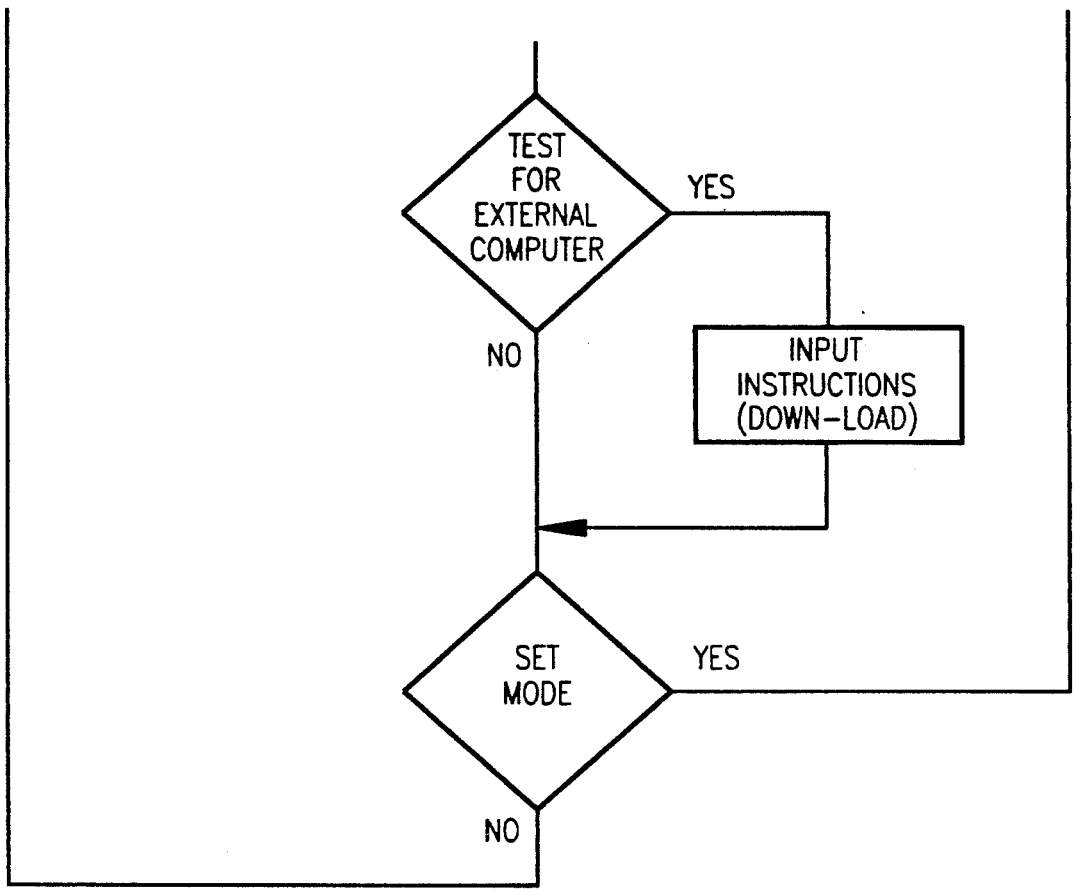
Figure 8I:
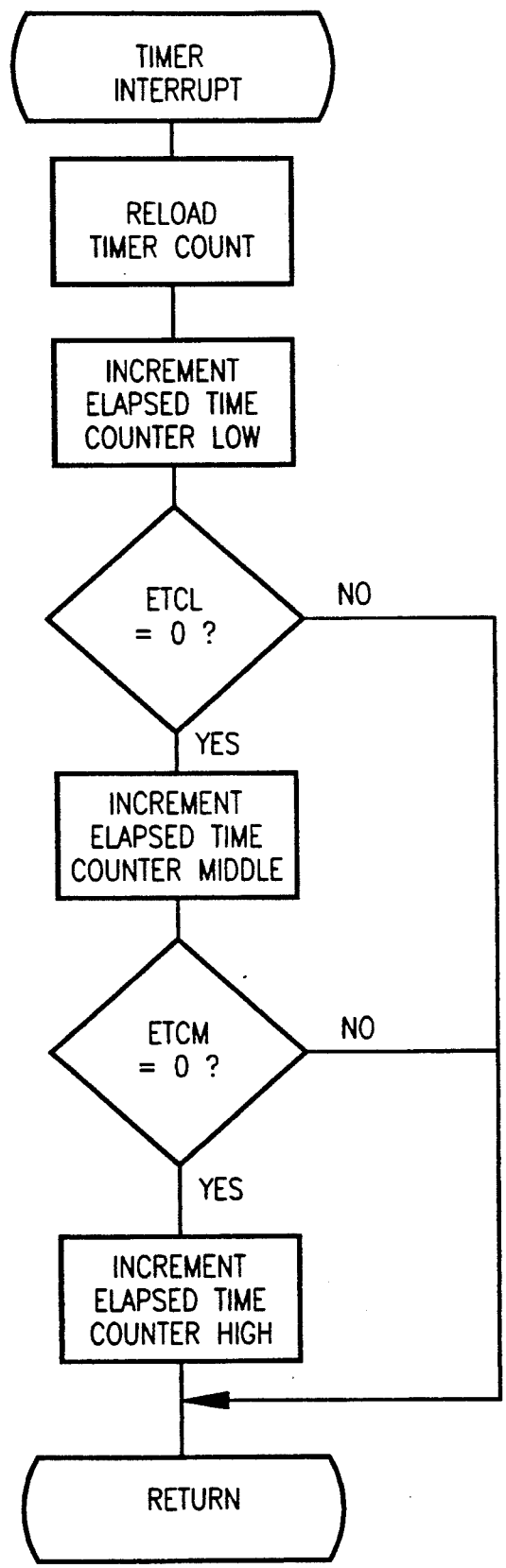
Figure 8J:
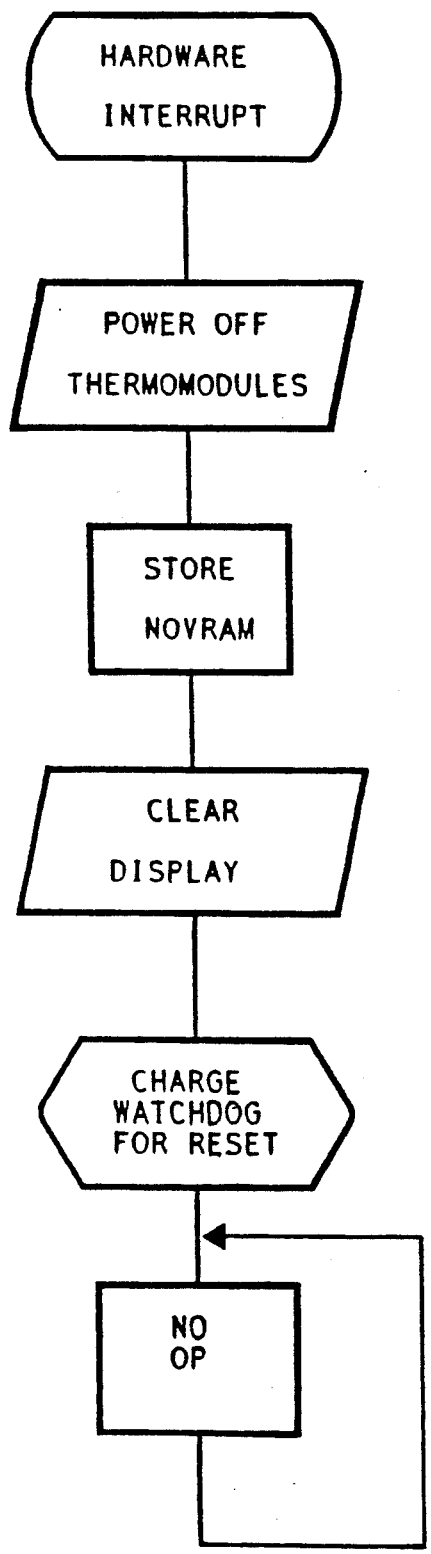

As best shown in FIG. 7, the temperature rate change control generally indicated as 400 include circuitry to generate a first and second signals where $|T_{SP}-T_S| \geq |T_S-T_{S+1}|$ defines the first signal
$|T_{SP}-T_S| < |T_S-T_{S+1}|$ defines the second signal
$T_{SP}$ being the set point temperature
$T_S$ being the solution temperature
$T_{S+1}$ being the previous solution temperature $T_{SP}$, $T_S$ and $T_{S+1}$ are data latches indicated as 402, 404 and 406 respectively with positive edge triggered clock inputs. The $T_{SP}$ value is the clocked in temperature set point value. $T_S$ value is the clocked in solution temperature value. $T_{S+1}$ value is the solution temperature delayed one clock cycle such as one minute. The $T_S$ value is subtracted from the $T_{SP}$ value in an asynchronous subtractor 408, this result is the delta $T_S$ value. The $T_{S+1}$ is subtracted from $T_S$ in a second asynchronous subtractor 410, the result is the delta $T_R$ value. The magnitude of delta $T_R$ is compared to the magnitude of delta $T_S$ in an asynchonous magnitude comparator 412. The negative output is high only when $|T_{SP}-T_S| < |T_S-T_{S+1}|$. The output of the comparator 412 is latched by a D-type flip-flop 414 clocked in on the negative edge of the clock pulse. The output signal, either the first or second signal, of the flip-flop 414 is fed to AND gate 416 where the signal is logically ANDed with the "active" signal from first order temperature control.

When the first thermal module control switch 226 receives a "heat" signal from the first order temperature control through conductor 268 and the enable signal from the second thermal module control switch 230 through 272, the first thermal module control switch 226 will generate a "heat" actuation signal fed to the thermal modules 16 through conductor 228.

When the first thermal module control switch 226 received a "cool" signal from the first order temperature control through conductor 268 and the enable signal from the second thermal module control switch 230 through 272, the first thermal module control switch 226 will generate a "cool" actuator signal fed to the thermal modules 16 through conductor 228.

To select solution or sensor mode operating mode, the solution key 118 or sensor key 120 is depressed while the indicator lamps are flashing. Once the operating mode is selected the set indicator lamp 114 will flash. The temperature increase key 124 or temperature decrease key 126 is then depressed to select the desired temperature. Wait ten seconds or press the set key 112. The four digit LED display 108 will show the actual temperature of the solution or sensor corresponding to the operating mode selected.

If the previous operating mode and temperature set point are desired, wait ten seconds after moving the power switch 138 to the ON position and the temperature control system will automatically recall the previous operating mode and temperature set point.

The Solution or Sensor temperature can be checked from either operating mode or by depressing and holding the sensor key 118 or solution key 120.

To change the operating mode, depress the solution key 116 or sensor key 120 and depress the set key 112. Wait ten seconds or depress the set key 112.

To change the temperature set point, depress either the solution key 116 or sensor key 120 and depress the set key 112. Actuate the temperature increase key 124 or temperature decrease key 126. Wait ten seconds or depress the set key 112.

The temperature control system will continue to operate in the selected operating mode without interruption or change unless one or more of the malfunctions or system continuations as previously described are experienced.

It will thus be seen that the objects set forth above, among those made apparent from the preceding description are efficiently attained and since certain changes may be in the above construction without departing from the scope of the invention, it is intended that all matter contained in the above description or shown in the accompanying drawing shall be interpreted as illustrative and not in a limiting sense.

It is also to be understood that the following claims are intended to cover all of the generic and specific features of the invention herein described, and all statements of the scope of the invention which, as a matter of language, might be said to fall therebetween.

Now that the invention has been described,
What is claimed is:

1. A temperature controlled fluid circulating system comprising a fluid circulating pump, a fluid flow sensor including means to sense the flow of fluid therethrough and to generate an obstructed signal when there is no fluid flow therethrough, a means to generate a pump operating signal and at least one thermal module operable in a heating or cooling state to monitor and control the temperature and flow of fluid circulated through a liquid circulation manifold, a display/control panel including input controls and at least one system indicator to select the system operating parameters and to provide a visual indication of the system status including fluid flow; and a micro control including logic circuitry to receive input signals from said display/control panel, said obstructed signal and said pump operating signal and to generate system control signals to control the operation of said temperature controlled fluid circulating system and system indicator to provide visual indication of system operations, said system indicator including an obstructed flow indicator lamp coupled to said micro control, said micro control including a fluid flow sensor indicator control means to receive said pump operating signal and said obstructed signal to generate a first signal to illuminate said obstructed flow indicator lamp when said fluid flow sensor generates said obstructed signal and said pump generates said pump signal.

2. The temperature controlled fluid circulating system of claim 1 wherein said display/control panel further including a normal flow indicator lamp coupled to said micro control and said fluid flow sensor including means to generate a flow signal in response to fluid flow therein said sensor indicator control means further including means to receive said flow signal to generate a second signal to illuminate said normal flow indicator lamp when said fluid flow sensor generates said flow signal and said pump generates said pump operating signal.

3. The temperature control fluid circulating system of claim 2 further including a system warning indicator coupled to said fluid flow sensor indicator control means, said fluid flow sensor indicator control means including circuitry to generate a third signal when said fluid flow sensor indicator control means has received said pump operating signal for a predetermined period of time and said obstructed signal is received from said fluid flow sensor to illuminate said system warning indicator.

4. The temperature control fluid circulating system of claim 1 further including a system warning indicator coupled to said fluid flow sensor indicator control means, said fluid flow sensor indicator control means including circuitry to generate a second signal when said fluid flow sensor indicator control means has received said pump operating signal for a predetermined period of time and said obstructed signal is received from said fluid flow sensor to illuminate said system warning indicator.

5. The temperature controlled fluid circulating system of claim 4 wherein said display/control panel further including a normal flow indicator lamp coupled to said micro control and said fluid flow sensor including means to generate a flow signal in response to fluid flow therein, said sensor indicator control means further including means to receive said flow signal to generate a second signal to illuminate said normal flow indicator lamp when said fluid flow sensor generates said flow signal and said pump generates said pump operating signal.

6. A temperature controlled fluid circulating system selectively operable in a first or second selected operating mode comprising a circulating pump, a first sensor to sense the temperature of the fluid including means to generate a first temperature signal corresponding to the temperature of the fluid and a second sensor disposed adjacent a liquid circulation manifold including means to generate a second temperature signal corresponding to the temperature adjacent said liquid circulation manifold and at least one thermal module operable in heating or cooling state to monitor and control the temperature of fluid circulated through said liquid circulation manifold, a display/control panel including input controls to select the system operating parameters including a selected operated temperature set point, and a micro control including logic circuitry to receive signals from said display/control panel and said first and second temperature signals from said first and second temperature sensors respectively and to selectively generate thermal module control signals to control the heating or cooling of said thermal module by comparing said selected operating temperature set point with the temperature sensed by said first sensor when operating in said first selected operating mode to selectively generate said thermal module control signals and by comparing said selected operating temperature set point with the temperature sensed by said second sensor when operating in said second selected operating mode to selectively generate said thermal module control signals, said temperature controlled fluid circulating system further operable in an alternate operating mode wherein said logic circuitry further includes an alternate operating mode logic means such that said temperature controlled fluid circulation system operates in said alternate operating mode when in said second selected operating mode and said second temperature signal exceeds a first predetermined temperature range.

7. The temperature control fluid circulating system of claim 6 wherein said alternate operating mode logic means further includes means to generate an alternate operating temperature set point to control the operation of the thermal module.

8. The temperature control fluid circulating system of claim 7 wherein said alternate operating temperature set point is substantially equal to said selected operating temperature set point when said selected operating temperature set point is greater than a first predetermined temperature.

9. The temperature control fluid circulating system of claim 7 wherein said alternate operating temperature set point is less than said selected operating temperature set point by a second predetermined amount when said selected operating temperature set point is less than said first predetermined temperature.

10. The temperature control fluid circulating system of claim 9 wherein said alternate operating temperature set point is at least a third predetermined temperature.

11. The temperature control fluid circulating system of claim 6 wherein said alternate mode logic means further includes means to generate an alternate operating temperature set point to control the operation of the thermal module; said alternate operating temperature set point being substantially equal to said selected operating temperature set point when said selected operating temperature set point is greater than a first predetermined temperature; said alternate operating temperature set point being less than said selected operating temperature set point by a second predetermined amount when said selected operating temperature set point is less than said first predetermined temperature and said alternate operating temperature set point at least a third predetermined temperature.

12. The temperature controlled fluid circulating system of claim 6 wherein said logic circuitry further includes logic means to compare said second temperature signal to said first predetermined temperature range when operating in said alternate operating mode and generating a control signal when said second temperature signal is within said first predetermined temperature range such that said temperature control fluid circulating system operates in said second selected operating mode.

13. A temperature controlled fluid circulating system comprising a circulating pump, a first sensor to sense the temperature of the fluid including means to generate a first temperature signal corresponding to the temperature of the fluid and at least one thermal module operable in a heating or cooling state to monitor and control the temperature and flow of fluid circulated through a liquid circulation manifold, a display/control panel including input controls to select the sytem opertaing parameters including a selected operating temperature set point, and a micro control including logic circuitry to receive input signals from said display/control panel and said first sensor system and to generate system control signals including a selected operating temperature set point signal corresponding to said selected operating temperature set point to control the operation of said temperature controlled fluid circulating system and a thermal module temperature control means to control the heating and cooling state of the thermal module wherein said thermal module temperature control means comprises temperature rate change control circuitry including means to selectively generate an enable signal when the rate of change of the fluid temperature during a predetermined period of time is less than the difference between the selected operating temperature set point and the fluid temperature to control the heating or cooling state of said thermal module.

14. The temperature controlled fluid circulating system of claim 13 wherein said temperature rate change control circuitry comprises a first subtractor to receive said selected operating temperature set point signal and said first temperature signal having means to generate a first output signal corresponding to the differences between said selected operating temperature set point signal and said first temperature signal, a memory means to receive and retain said first temperature signal for a predetermined period of time and a second subtractor to receive said first temperature signal from said first sensor and said first temperature signal from said memory means having means to generate a second output signal corresponding to the difference between said first temperature signal from said first sensor and said first temperature signal from said memory means, said temperature rate change further including a magnitude comparator operatively coupled to said first subtractor and said second subtractor to receive said first and second output signals therefrom, said magnitude comparator including logic means to generate said enable signal when said second signal is greater than said first signal.

15. A temperature controlled fluid circulating system selectively operable in a first or second selected operating mode comprising a circulation pump and at least one thermal module operable in heating or cooling state to monitor and control the temperature of fluid circulated through a liquid circulation manifold, a display/control panel including a first and second operating mode key each movable between a first and second position to generate a first operating mode signal when said first operating mode key is in said first position and to generate a second operating mode signal when said second operating mode key is in said first position, and a micro control including logic circuitry to selectively receive said first and second operating mode signals from said display/control panel and to generate a temperature control signal corresponding to a first predetermined temperature when in said first operating mode and a temperature control signal corresponding to a second predetermined temperature when in said second operating mode to control the heating or cooling of said thermal module.

16. The temperature controlled fluid circulating system of claim 15 wherein said display/control panel further includes a temperature select key movable between a first and second position to generate an operating temperature signal corresponding to a selected operating temperature set point when in said first postion and said logic circuitry further includes means to receive said operating temperature signal and generate a temperature control signal corresponding to said selected operating temperature set point to control the heating or cooling of the thermal module.

17. The temperature controlled fluid circulating system of claim 16 wherein said display/control panel further includes a power switchi movable between an off and on position and said logic circuitry further includes means to generate a temperature control signal, said selected operating temperature set point and said selected operating mode to control the heating or cooling of the thermal module when said first and second operating mode set keys remain in said second position for more than a predetermined period of time when said power switch is moved from said off position to said on position.

* * * * *